(12) United States Patent
Kobayashi et al.

(10) Patent No.: US 7,850,801 B2
(45) Date of Patent: *Dec. 14, 2010

(54) LAYERED FILM FABRICATION METHOD, LAYERED FILM DEFECT DETECTION METHOD, LAYERED FILM DEFECT DETECTION DEVICE, LAYERED FILM, AND IMAGE DISPLAY DEVICE

(75) Inventors: Takamasa Kobayashi, Ibaraki (JP); Michihiro Hagiwara, Ibaraki (JP); Yuuki Yano, Ibaraki (JP); Kouji Shizen, Ibaraki (JP)

(73) Assignee: Nitto Denko Corporation, Ibaraki-shi, Osaka (JP)

( * ) Notice: Subject to any disclaimer, the term of this patent is extended or adjusted under 35 U.S.C. 154(b) by 160 days.

This patent is subject to a terminal disclaimer.

(21) Appl. No.: 12/159,928

(22) PCT Filed: Jan. 10, 2007

(86) PCT No.: PCT/JP2007/050121
§ 371 (c)(1),
(2), (4) Date: Jul. 2, 2008

(87) PCT Pub. No.: WO2007/080867
PCT Pub. Date: Jul. 19, 2007

(65) Prior Publication Data
US 2009/0288754 A1    Nov. 26, 2009

(30) Foreign Application Priority Data
Jan. 11, 2006  (JP) ............................. 2006-003856
Dec. 18, 2006  (JP) ............................. 2006-340274

(51) Int. Cl.
*B32B 38/00*    (2006.01)

(52) U.S. Cl. .................. 156/64; 156/378; 156/379; 356/239.1; 356/239.2; 356/237.6; 356/432; 356/433; 356/434; 349/74; 349/75; 349/76; 349/117; 349/118; 349/119; 349/120

(58) Field of Classification Search ................ 156/64, 156/378, 379; 356/239.1, 239.2, 237.6, 432, 356/433, 434; 349/74, 75, 76, 117, 118, 349/119, 120
See application file for complete search history.

(56) References Cited

U.S. PATENT DOCUMENTS
6,034,754 A * 3/2000 Sato et al. .................. 349/102
(Continued)

FOREIGN PATENT DOCUMENTS
CN    1412582 A    4/2003
(Continued)

OTHER PUBLICATIONS
International Search Report of PCT/JP2007/050121, date of mailing Apr. 17, 2007.
(Continued)

*Primary Examiner*—Kat Wyrozebski
*Assistant Examiner*—Joshel Rivera
(74) *Attorney, Agent, or Firm*—Westerman, Hattori, Daniels & Adrian, LLP

(57) ABSTRACT

A defect detection method of a layered film having a polarizing plate and an optical compensation layer includes steps of: applying light from a light source arranged at the polarizing plate layer side of the film surface of the layered film; a step of imaging a transmitting light image of the layered film by an imaging unit arranged at the optical compensation layer side of the film surface; and a defect detection step for detecting a defect existing on the layered film according to the transmitting light image captured by the imaging unit. The imaging unit performs imaging via an inspection polarizing filter arranged on the optical path between the light source and the imaging unit and adjacent to the imaging unit; and an inspection phase difference filter arranged on the optical path between the light source and the imaging unit and between the inspection polarizing filter and the layered film.

7 Claims, 10 Drawing Sheets

U.S. PATENT DOCUMENTS

| | | | |
|---|---|---|---|
| 6,650,410 B2 | 11/2003 | Shimoda | |
| 2003/0103186 A1 | 6/2003 | Sasaki et al. | |
| 2004/0125375 A1* | 7/2004 | Some | 356/369 |
| 2009/0009864 A1* | 1/2009 | Kobayashi et al. | 359/485 |

FOREIGN PATENT DOCUMENTS

| | | | |
|---|---|---|---|
| JP | 2001-159582 A | 6/2001 | |
| JP | 2001-324453 A | 11/2001 | |
| JP | 2005-9919 A | 1/2005 | |
| JP | 2005-337814 A | 12/2005 | |

OTHER PUBLICATIONS

Notification of Transmittal of Translation of the International Preliminary Report on Patentability (Form PCT/IB/338) of International Application No. PCT/JP2007/050121 mailed Jul. 24, 2008 with Forms PCT/IB/373, PCT/IB/326, PCT/ISA/237 and English translation of PCT/ISA/237.

Chinese Office Action dated Jul. 14, 2010, issued in corresponding Chinese Patent Application No. 200780001727.

* cited by examiner (a)

(b)

INITIAL DATA OF FIG. 5

DATA AFTER 48 HOURS OF FIG. 5

INITIAL DATA OF FIG. 10(b4)

DATA AFTER 48 HOURS OF FIG. 10(b4)

LAYERED FILM FABRICATION METHOD, LAYERED FILM DEFECT DETECTION METHOD, LAYERED FILM DEFECT DETECTION DEVICE, LAYERED FILM, AND IMAGE DISPLAY DEVICE

TECHNICAL FIELD

The present invention relates to a fabrication method of a layered film in which at least a polarizing plate and an optical compensation layer are layered, a layered film defect detection method, a layered film defect detection device, a layered film, and an image display device.

BACKGROUND ART

The layered film in which a retardation film (corresponding to optical compensation method) is layered on a polarizing plate via an adhesive layer is known as a layered film of the present invention. A layered configuration example of the layered film is shown in FIG. 12. A layered film 11 is configured by a polarizing plate 1 including a polarizer 1a and a protective film 1b layered on both sides thereof via an adhesive layer, and a retardation film 2 (or retardation layer directly layered on one side of the polarizing plate 1) layered on one side of the polarizing plate 1 via an adhesive layer 2a. When inspecting defects such as foreign substances, scratches, nicks and the like existing on the polarizing plate 1, light is irradiated from an appropriate light source onto the polarizing plate 1, a reflected light image or a transmitted light image is acquired via an imaging unit such as a line sensor camera or a two-dimensional TV camera, and defect detection is performed based on the acquired image data. When inspecting the polarizing plate, the image data is acquired with an inspection polarization film interposed in the middle of a light path between the light source and the imaging unit. Normally, a polarizing axis (e.g., polarized absorption axis) of the inspection polarization filter is arranged in a state (cross Nicol) orthogonal to a polarizing axis (e.g., polarized absorption axis) of the polarizing plate 1 to be inspected. According to the cross Nicol arrangement, an all-black image is input from the imaging unit if defect does not exist, and the relevant portion does not become black if the defect exists. Therefore, defect can be detected by setting an appropriate threshold value.

In the layered film in which the optical compensation layer having retardation exists in addition to the polarizer, however, the optical axis shifts when the light from the light source passes through the optical compensation layer, and the polarizer and the inspection polarization filter will not be in a substantially cross Nicol state. As a result, the defect inspection of the polarizing plate cannot be accurately performed.

A polarizing plate inspection device disclosed in Patent Document 1 is known as a layered film (polarizing plate with protective film) defect detection device for solving the above problems. The polarizing plate inspection device is arranged with a light source arranged on one side of a polarizing plate; an imaging unit arranged on the other side of the polarizing plate and imaging a transmitted light image of the polarizing plate; and an inspection polarization filter and an inspection retardation plate arranged in a light path between the polarizing plate and the light source. Using the inspection polarization filter for converting the light from the light source to a linear polarized light, the linear polarized light is input to the polarizing plate with protective film, and defect detection is performed based on the transmitted light image. Furthermore, a retardation plate for compensating birefringence of the light caused by the protective film is arranged on the light path transmitting through the polarizing plate with protective film from the light source. The change in phase by the protective film having retardation can be canceled and the birefringence of the light by the protective film can be compensated by separately arranging the retardation plate. Furthermore, a configuration example of arranging a variable polarization optical element in which the phase angle of the light is adjustable by voltage to compensate the birefringence by the protective film that differs slightly among products is also disclosed.

Patent Document 1: Japanese Laid-Open Patent Publication No. 2005-9919

DISCLOSURE OF THE INVENTION

Problems to be Solved by the Invention

However, in recent years, numerous drawbacks arise with the method described in Patent Document 1 as the layered film including the polarizing plate becomes larger.

First, the light source becomes larger to uniformly irradiate light to the film surface as the layered film to be inspected becomes larger. Accompanied therewith, an inspection filter having an area suited to be able to cover the light source is required in the configuration shown in Patent Document 1 and the like. For instance, in order to inspect a film having a length in the width direction of 1500 mm, a light source of about 1800 mm width is generally necessarily adopted to uniformly irradiate light even to the ends, and similarly, an inspection filter of greater than or equal to 1800 mm width is necessarily adopted. Thus, maintenance of the inspection filter is very difficult. The inspection filter may be rotated in accordance with the polarizing axis and the optical axis that differ for every product, but in this case, an inspection filter of the same size as the light source is necessarily adopted, and the task necessary for maintenance such as replacement and rotation becomes more difficult.

In the configuration shown in Patent Document 1, the filter tends to easily degrade by heat and light energy since the inspection filter is close to the light source and is always exposed in a constant state. As a result, not only is cost necessary for replacing the inspection filter, but also outflow of defective product increases since the defect detection accuracy degrades with degradation of the inspection filter.

In view of the above situations, the present invention aims to provide a layered film fabrication method, a layered film defect detection method, and a layered film defect detection device in which defect detection leakage of the layered film is extremely small and a stable quality can be provided over a long period by appropriately arranging a member to be arranged in an imaging light path when performing a defect inspection of a layered film including a polarizing plate by using an inspection polarizing filter and an inspection retardation filter.

Means for Solving the Problems

In order to solve the above problems, a layered film fabrication method of the present invention relates to a layered film fabrication method including the steps of fabricating a layered film by layering at least a polarizing plate and an optical compensation layer, and performing defect inspection of the fabricated layered film; wherein the defect inspection step includes the steps of irradiating a light on the layered film from a light source arranged on the polarizing plate layered side of the layered film, imaging a transmitted light image of the layered film by an imaging unit arranged on the optical compensation layer side of the layered film, and detecting a defect existing in the layered film based on the transmitted light image imaged by the imaging unit; and the imaging by the imaging unit is performed via an inspection polarization filter arranged adjacent to the imaging unit on a light path between the light source and the imaging unit, and an inspection retardation filter arranged between the inspection polarization filter and the layered film on the light path between the light source and the imaging unit.

In order to solve the above problems, a layered film defect detection method of the present invention relates to a defect detection method of a layered film in which at least a polarizing plate and an optical compensation layer are layered; the method including the steps of irradiating a light on the layered film from a light source arranged on the polarizing plate layered side of the layered film; imaging a transmitted light image of the layered film by an imaging unit arranged on the optical compensation layer side of the layered film; and detecting a defect existing in the layered film based on the transmitted light image imaged by the imaging unit; wherein the imaging by the imaging unit is performed via an inspection polarization filter arranged adjacent to the imaging unit on a light path between the light source and the imaging unit, and an inspection retardation filter arranged between the inspection polarization filter and the layered film on the light path between the light source and the imaging unit.

The effects of the layered film defect detection device of the above configuration will be described. In the layered film to be inspected, at least the polarizing plate and the optical compensation layer are layered. The light source is arranged on the polarizing plate side of the film surface of the layered film, and the imaging unit (e.g., line sensor camera) is arranged on the optical compensation layer side. The inspection polarization filter and the inspection retardation filter are arranged in the light path between the light source and the imaging unit. The inspection polarization filter is arranged adjacent to the imaging unit, and the inspection retardation filter is arranged between the inspection polarization filter and the layered film. The light irradiated from the light source is polarized by the inspection polarization filter, and the transmitted light image of the layered film is input to the imaging unit. The inspection retardation filter acts in a direction of canceling out the retardation caused by the optical compensation layer. The defect detection unit performs defect detection based on the image data of the input transmitted light image. Numerous techniques and algorithms are known for performing defect detection, and are not limited to a specific detection method.

According to the above configuration, since the inspection polarization filter is arranged adjacent to the imaging unit, it is positioned on the side opposite to the light source with the layered film sandwiched between. Therefore, influence of light and heat by the light source can be alleviated, the polarization filter becomes less likely to degrade, and the desired characteristics can be maintained. This is the same for the inspection retardation filter. Furthermore, since the layered film to be inspected is to be sequentially replaced, influence on degradation by light and heat is small compared to the inspection filter that is always at a constant position. As a result, there can be provided the layered film fabrication method and defect detection method in which members to be arranged in the imaging light path are arranged in an appropriate order when performing defect inspection of the layered film including the polarizer by using the inspection polarization filter and the inspection retardation filter.

Furthermore, the configuration of the present invention results in the particularly significant effect in fabricating a large layered film having a length in the width direction of greater than or equal to 1350 mm, and contributes greatly to enhancing the accuracy of defect inspection in the layered film having a large area, and achieving efficiency with enlargement of the device.

The layered film fabrication method according to the present invention includes the steps of fabricating a layered film by layering at least a polarizing plate and a retardation layer, and performing defect inspection of the layered film, and thus outflow of defective products with defect is prevented.

In order to solve the above problem, a layered film defect detection device of the present invention relates to a defect detection device of a layered film in which at least a polarizing plate and an optical compensation layer are layered; the device including a light source arranged on the polarizing plate layered side of the layered film and irradiating a light on the layered film; an imaging unit arranged on the optical compensation layer side of the layered film and imaging a transmitted light image of the layered film; a defect detection unit for detecting a defect existing in the layered film based on the transmitted light image imaged by the imaging unit; an inspection polarization filter arranged adjacent to the imaging unit on a light path between the light source and the imaging unit; and an inspection retardation filter arranged between the inspection polarization filter and the layered film on the light path between the light source and the imaging unit.

According to such configuration, there can be provided the layered film defect detection device in which members to be arranged in the imaging light path are arranged in an appropriate order when performing defect inspection of the layered film including the polarizer by using the inspection polarization filter and the inspection retardation filter.

It is preferable that the optical compensation layer according to the present invention is a retardation layer having an orientation angle variation of retardation controlled to be within 4° and the inspection retardation filter has an inspection retardation having same characteristics as the retardation layer.

According to such configuration, the shift in retardation can be efficiently canceled. The orientation angle variation indicates the retardation variation in the film surface, and is an, index representing the extent of shift from the desired orientation direction (orientation angle) of molecules for controlling the retardation of the optical compensation layer. The present invention can be preferably applied in the layered film including the optical compensation layer used in the final product such as the image display device and the layered film including the optical compensation layer which orientation angle variation is controlled to smaller than or equal to 4°, whereby inspection of satisfactory accuracy can be performed. The orientation angle variation is obtained by measuring the orientation angle at about three to six points equally in the width direction of the film, and determining the difference between the maximum value and the minimum value, wherein the orientation angle can be measured with a commercially available retardation measurement apparatus such as KOBRA-21ADH manufactured by Oji Keisoku Co.

Preferably, the optical compensation layer according to the present invention includes a discotic liquid crystal layer, and the inspection retardation filter is an inspection discotic liquid crystal layer having the same characteristics. The shift in retardation thus can be efficiently canceled.

Furthermore, in the present invention, it is preferable that a first optical axis adjustment unit for adjusting a relative angle position of a polarizing axis of the inspection polarization filter and a polarizing axis of the polarizing plate is arranged. According to such configuration, an optimum relative angle position can be found, and the inspection polarization filter can be arranged at an appropriate position with respect to each type of product by adjusting the polarizing axis of the inspection polarization filter depending on the type of layered film and the orientation angle variation in the film surface.

Moreover, in the present invention, it is preferable that a second optical axis adjustment unit for adjusting a relative angle position of an optical axis of the inspection retardation filter and an optical axis of the optical compensation layer is arranged. According to such configuration, an optimum relative angle position can be found, and the inspection retardation filter can be arranged at an appropriate position with respect to each type of product by adjusting the optical axis of the inspection retardation filter depending on the type of layered film and the orientation angle variation in the film surface.

Figure 1:
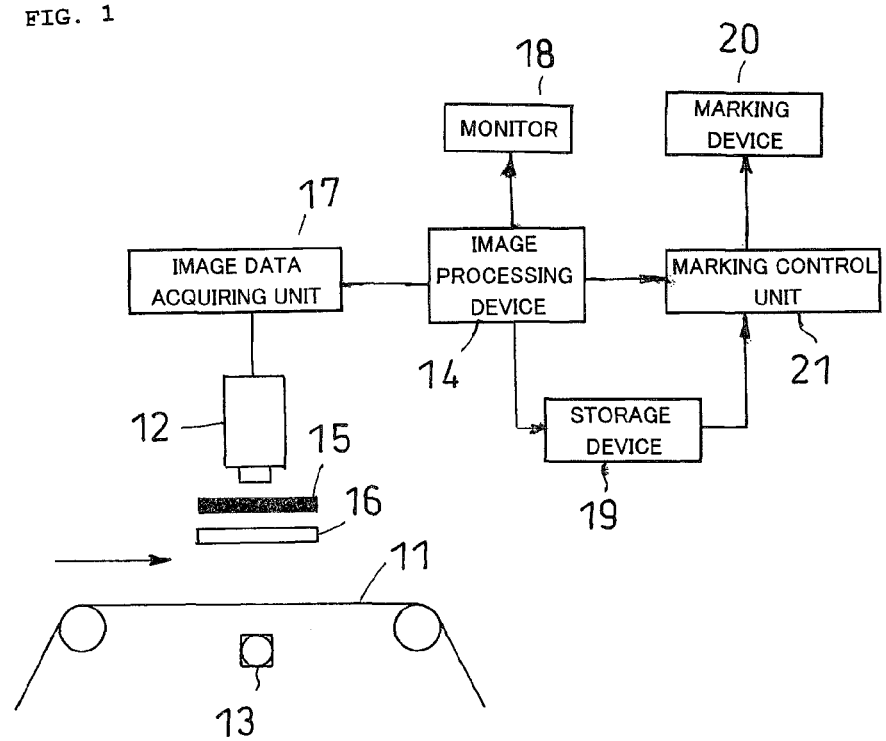
FIG. 1 is a schematic view showing a configuration of a layered film defect detection device.

DESCRIPTION OF SYMBOLS 1a polarizer
1b protective film
2 retardation film (optical compensation layer)
11 layered film
12 imaging unit
13 light source
14 image processing device
15 inspection polarization filter
16 inspection retardation filter
17 image data acquiring unit
18 monitor
19 storage device
20 marking device
21 marking control unit
31 first optical axis adjustment unit
32 second optical axis adjustment unit

BEST MODE FOR CARRYING OUT THE INVENTION

Figure 12:
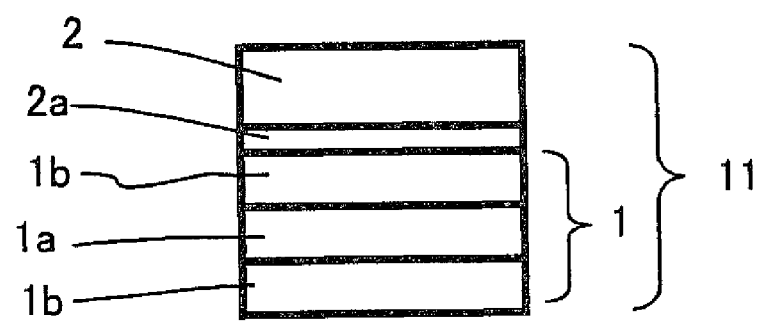
FIG. 12 is a view showing a layered configuration example of the layered film.

Suitable embodiments of layered film defect detection method and device according to the present invention will now be described with reference to the figures. FIG. 1 is a schematic view showing a configuration of the defect detection method and device. As shown in FIG. 12, a layered film 11 to be inspected is configured by at least a polarizing plate 1 and an optical compensation layer to be layered on the polarizing plate 1. Retardation film and orientation liquid crystal layer are listed as the optical compensation layer.

In FIG. 1, the layered film 11 is pulled out from a state wound to a roll (not shown), and conveyed from the left side to the right side of the figure. A light source 13 for inspection is arranged on one side (lower side in FIG. 1) of a film surface of the layered film 11. The light source 13 may be fluorescent lamp, halogen lamp, metal halide lamp, LED, or the like, and the appropriate light source 13 is selected depending on the type of layered film 11 to be inspected. Planar shape, light bulb shape, rectangular shape in the film width direction, and the like may be appropriately adopted for the shape of the light source 13.

Figure 2:
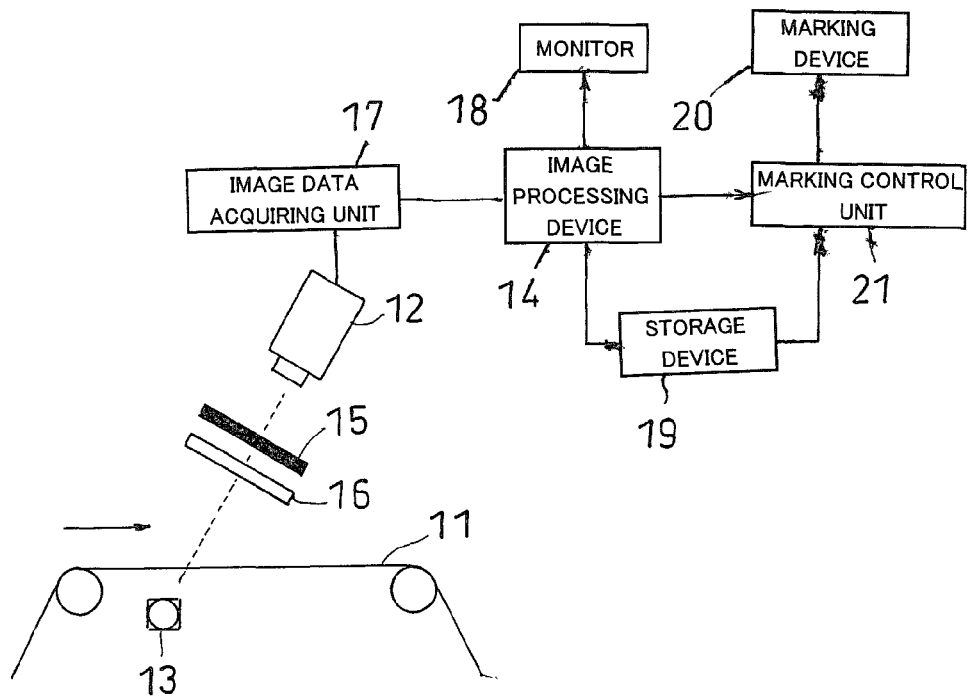
FIG. 2 is a schematic view showing another configuration of a layered film defect detection device.

An imaging unit 12 is configured by a line sensor camera, a two-dimensional TV camera, or the like. One or a plurality of imaging units 12 is arranged along the width direction depending on the size in the width direction of the layered film 11. An image processing device 14 has a function of performing defect detection of the polarizing plate 1 by performing image processing on the image data imaged by the imaging unit 12. A light path connecting the imaging unit 12 and the light source 13 is set to be perpendicular to the film surface of the layered film 11, but the light path may be inclined with respect to the film surface as shown in FIG. 2 due to the restriction in installing locations of the light source 13 and the imaging unit 12.

As shown in FIG. 1, an inspection polarization filter 15 is arranged on the front surface of the imaging unit 12. A polarizing axis L2 (see FIG. 3) of the inspection polarization filter 15 is arranged to be in a cross Nicol position relationship with a polarizing axis L1 of a polarizer of the polarizing plate 1. According to the cross Nicol arrangement, an all-black image is input from the imaging unit if the defect does not exist, and the relevant portion does not become black if the defect exists. Therefore, the defect can be detected by setting an appropriate threshold value. However, since the optical compensation layer is provided on the polarizing plate 11, the optical axis shifts when the light from the light source passes through the optical compensation layer, and the cross Nicol state cannot be substantially obtained. The inspection polarization filter 15 used is similar to the polarizing plate 1 and is defect-free.

Since the optical compensation layer has an in-plane retardation, the light quantity to be input to the imaging unit 12 differs depending on the position of the layered film 11, and the image to be input to the imaging unit 12 also differs in brightness between the central part and the ends. The contrast between the defect part and the other image portions is ideally constant regardless of the location in the image, but the contrast becomes unequal due to the above reasons. As a result, determination might be made as pass although a luminescent point such as pin hole that is apparently large exists, and on the other hand, erroneous determination might be made as fail although the defect is a very small defect that can be determined as pass. That is, the defect detection ability needs to be constant between the central part and the ends of the image.

In view of the above problems, an inspection retardation filter 16 is arranged adjacent to the inspection polarization filter 15. The inspection retardation filter 16 is arranged between the inspection polarization filter 15 and the layered film 11 while being adjacent to the inspection polarization filter 15. The inspection device can be miniaturized and the maintenance property thereof can be enhanced by adjacent arrangement. The inspection retardation filter 16 preferably has the same property (e.g., same material, thickness, retardation) as the optical compensation layer configuring the layered film 11. For instance, if the optical compensation layer is a triacetyl cellulose film (polarizer protective film) with discotic liquid crystal layer, a film including the inspection discotic liquid crystal layer having the same property is used. Accordingly, the retardation caused by the presence of the optical compensation layer is canceled (or suppressed), and the defect detection is stably performed.

Figure 3:
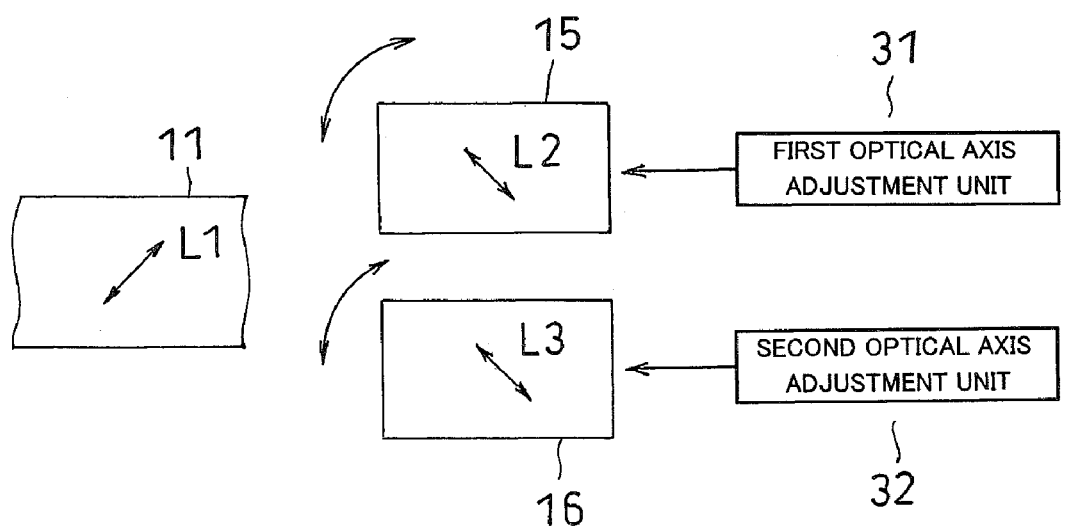
FIG. 3 is a view illustrating an adjustment mechanism of polarizing axes of an inspection polarization filter and an inspection retardation filter.

FIG. 3 is a view illustrating adjustment of the polarizing axis L2 of the inspection polarization filter 15 and an optical axis L3 of the inspection retardation filter 16. A first optical axis adjustment unit 31 provides a mechanism for rotatably driving the inspection polarization filter 15 in plane. The center of rotation coincides with a light path connecting the light source 13 and the imaging unit 12. Similarly, a second optical axis adjustment unit 32 provides a mechanism for rotating the inspection retardation filter 16 in plane. The center of rotation coincides with a light path connecting the light source 13 and the imaging unit 12. The inspection polarization filter 15 and the inspection retardation filter 16 can be arranged in a fixed state, but the polarizing axis of the polarization filter can be adjusted with respect to the polarizing axis L1 of the polarizing plate 1, or the optical axis of the inspection retardation filter 16 can be adjusted with respect to the optical axis of the optical compensation layer in view of orientation angle variation of the optical compensation layer by being rotatable, whereby enabling the inspection polarization filter 15 and the inspection retardation filter 16 to be set in an optimum position.

Since there are various types of the optical compensation layer configuring the layered film 11 to be inspected, the optimum arrangement of the inspection polarization filter 15 and the inspection retardation filter 16 differs depending on the type of the layered film 11. Appropriate defect detection can be performed depending on the type of the layered film 11 by arranging the mechanism for horizontally rotating the inspection polarization filter 15 and the inspection retardation filter 16 as shown in FIG. 3. In this case, it is preferable to stamp or print the rotation angle, or attach a mark to the inspection polarization filter 15 and the inspection retardation filter 16 to know how many times the inspection polarization filter 15 and the inspection retardation filter 16 have been rotated with respect to the reference position. A relationship between the type of the layered film 11 and the angle position may be stored in a memory to enable automatic setting to a predetermined angle position by the first optical axis adjustment unit 31 and the second optical axis adjustment unit 32.

As shown in FIG. 1, an image signal imaged by the imaging unit 12 is converted to image data digitalized by an image data acquiring unit 17, and sent to an image processing device 14. The image processing device 14 is configured with the software function as the core, and has a function of a defect detection unit. The light quantity detection unit detects the position where the brightness of the imaged image becomes a minimum. The defect detection unit 14b performs defect detection by image processing the image data acquired by the imaging unit 12, wherein a known method is used for the defect detection algorithm. For instance, since the luminance of the location where the defect exists becomes bright, defect can be extracted by binarizing the acquired image data with a threshold value of a predetermined level. The feature quantity such as area, length, width, and luminance of the extracted defect are calculated, and one or a plurality of the feature quantity is selected to determine a pass/fail.

A monitor 18 can project the image imaged by the imaging unit 12 to visually check the presence of the defect. A storage device 19 stores position coordinate, feature quantity of the defect, and the like when the defect is detected. A marking device 20 is a device for marking the defect position when the defect is extracted. A marking control unit 21 controls the operation of the marking device 20. Specifically, the marking device 20 is controlled so that the defect position (or end in the width direction of the layered film 11) is accurately marked based on the coordinate signal of the defect position stored in the storage device 19. A device having a known configuration may be used for the marking device 20. The marking may be performed with a magic marker. The feature quantity (defect information) of the defect may be printed on the layered film 11 with an inkjet printer and the like.

Figure 4:
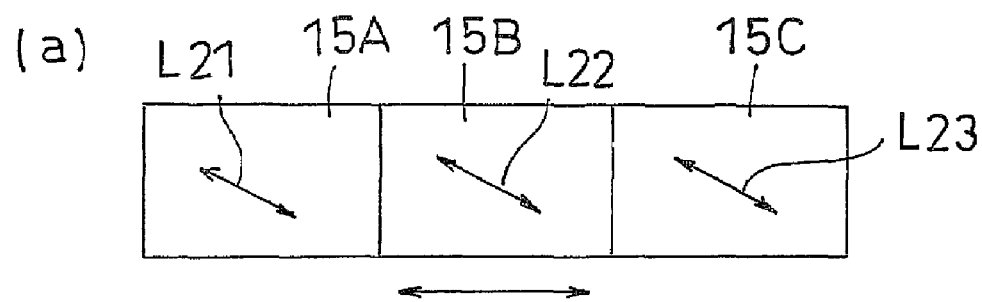
FIG. 4 is a view illustrating another embodiment of an adjustment mechanism of a polarizing axis of the inspection polarization filter.
Figure 4:
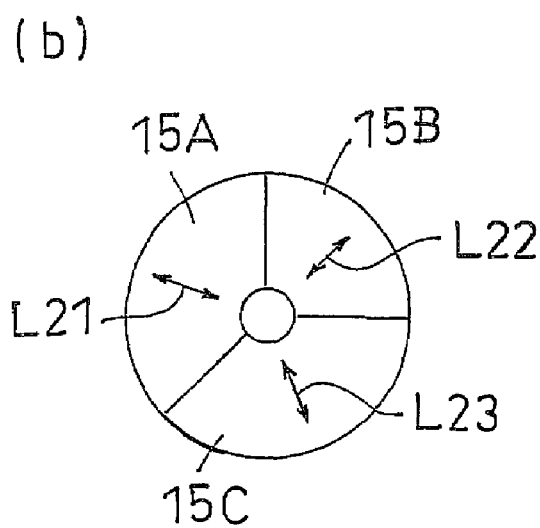

FIG. 4 is a view showing another embodiment of the inspection polarization filter 15. FIG. 4(a) shows three inspection polarization filters 15A, 15B, and 15C having different polarizing axes connected in a line, wherein the relative angle position of the polarizing axes can be adjusted by arranging one of the polarization filters 15 on the light path. The polarizing axes L21, L22, L23 of the respective inspection polarization filters 15A, 15B, 15C differ slightly from each other. FIG. 4(b) shows three polarization filters 15A, 15B, 15C having different polarizing axes connected in a circumferential direction. In the example of FIG. 4, the number of polarization filter 15 is three, but is not limited thereto, and can be appropriately determined. The similar construction can be adopted to the inspection retardation filter 16.

Figure 5:
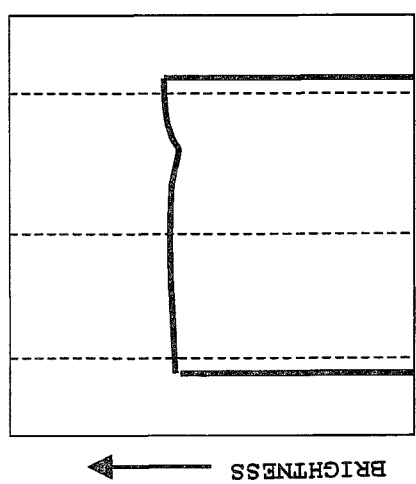
FIG. 5 is a view showing an image signal of when a polarizing plate including a retardation layer is imaged.

Specific examples will now be described. A film in which an optical compensation layer (WV film "WVA038" of orientation angle variation of 1.0° manufactured by Fuji Film Co.) is layered on one side of a commercially available polarizing plate is used for the layered film 11. A halogen lamp is used for the light source 13, and a line sensor camera is used for the imaging unit 12. The arrangement of each member in the imaging light path is carried out according to the arrangement configuration of FIG. 1. First, as the layered film 11 to be inspected, the retardation film in which the retardation is controlled is layered, and defect-free film is used. The inspection polarization filter 15 and the inspection retardation filter 16 are arranged in order from the imaging unit 12 side on the front surface of the imaging unit 12. An image signal obtained by the imaging unit 12 is shown in FIG. 5. Although slight fluctuation exists between the central part and the ends of the image, the luminance in the viewing direction (main scanning direction) of the line sensor camera is substantially constant, and stable inspection can be performed regardless of at which position the defect exists.

The light source 13 used in verification is halogen light source device MHF-100 (100 Watts) manufactured by Moritex Co., wherein the brightness of the light source (brightness of measurement at 30 cm above the light source) is adjusted to be 6060 cd/m².

Figure 6:
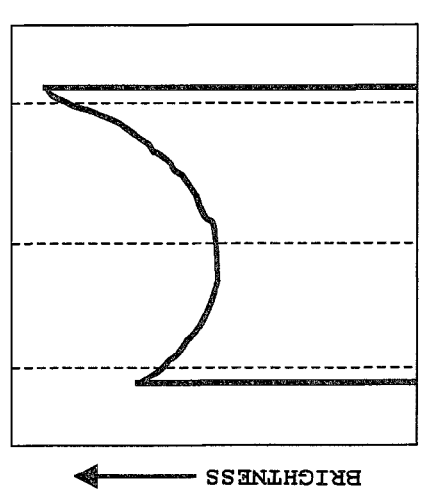
FIG. 6 is a view showing an image signal when imaged using the polarization filter arranged in cross Nicol with respect to the polarizing plate including the retardation layer.

The image signal obtained in the same condition as the above example except that the inspection retardation filter 16 is not arranged is shown in FIG. 6. Compared to FIG. 5, the luminance at the central part is low, and the luminance becomes higher towards the periphery. That is, since the difference in luminance between the central part and the ends is large and unstable, pass/fail decision of the defect cannot be stably made.

Figure 7:
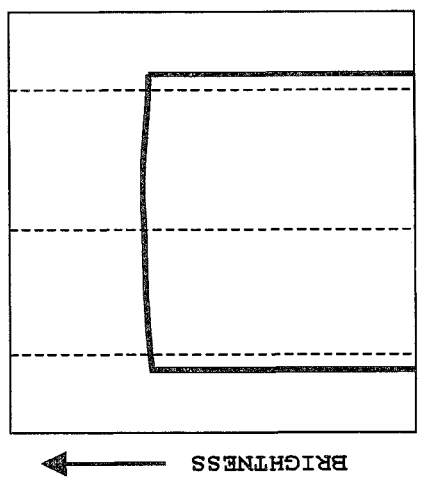
FIG. 7 is a view showing an image signal when imaged using the polarization filter arranged in cross Nicol with respect to the polarizing plate not including the retardation layer.

Furthermore, the image signal of when only the inspection polarization filter 15 is arranged using only that in which defect is not present in the polarizing plate 1 is shown in FIG. 7.

The area (pixel unit) of when the defect is detected at the position of the central part of FIG. 7 as an area "20" at the positions on the left end, middle, and right end under the conditions of FIGS. 5 to 7 is shown in table 1. Inspector manufactured by Matrox Co. is used to calculate the area.

TABLE 1

|  | FIG. 5 | FIG. 6 | FIG. 7 |
|---|---|---|---|
| Left end | 21 | 14 | 21 |
| Middle | 18 | 30 | 20 |
| Right end | 17 | 0 | 21 |

In the case of FIG. 5 or FIG. 7, the area is substantially the same even if the defect is present at any position, but in the case of FIG. 6, the area is sometimes "0" depending on the position, and thus stable defect detection cannot be performed. Therefore, in the case in which the inspecting object is only the polarizing plate 1 (case in which the retardation layer is not layered on the polarizing plate 1), stable inspection can be performed with only the inspection polarization filter 15 without particularly using the inspection retardation filter 16; and in the case of the layered film 11 in which the retardation layer is layered, stable inspection can be performed by further arranging the inspection retardation filter 16 having the same properties as the retardation layer, and arranging the inspection polarization filter 15 and the inspection retardation filter 16 in this order from the imaging unit 12 side.

Figure 8:
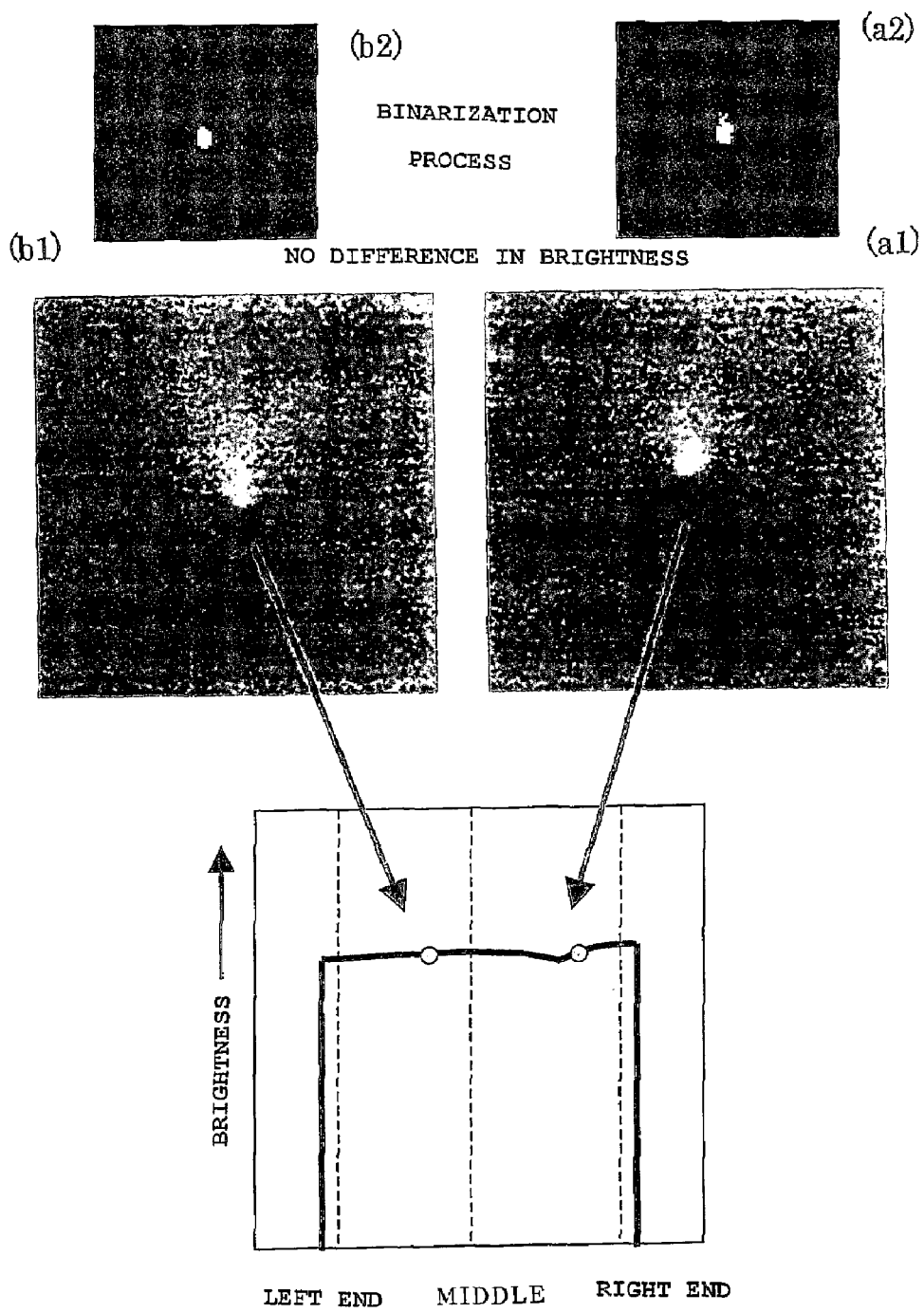
FIG. 8 is a view showing an original image and a binary image in the example of FIG. 5.
Figure 9:
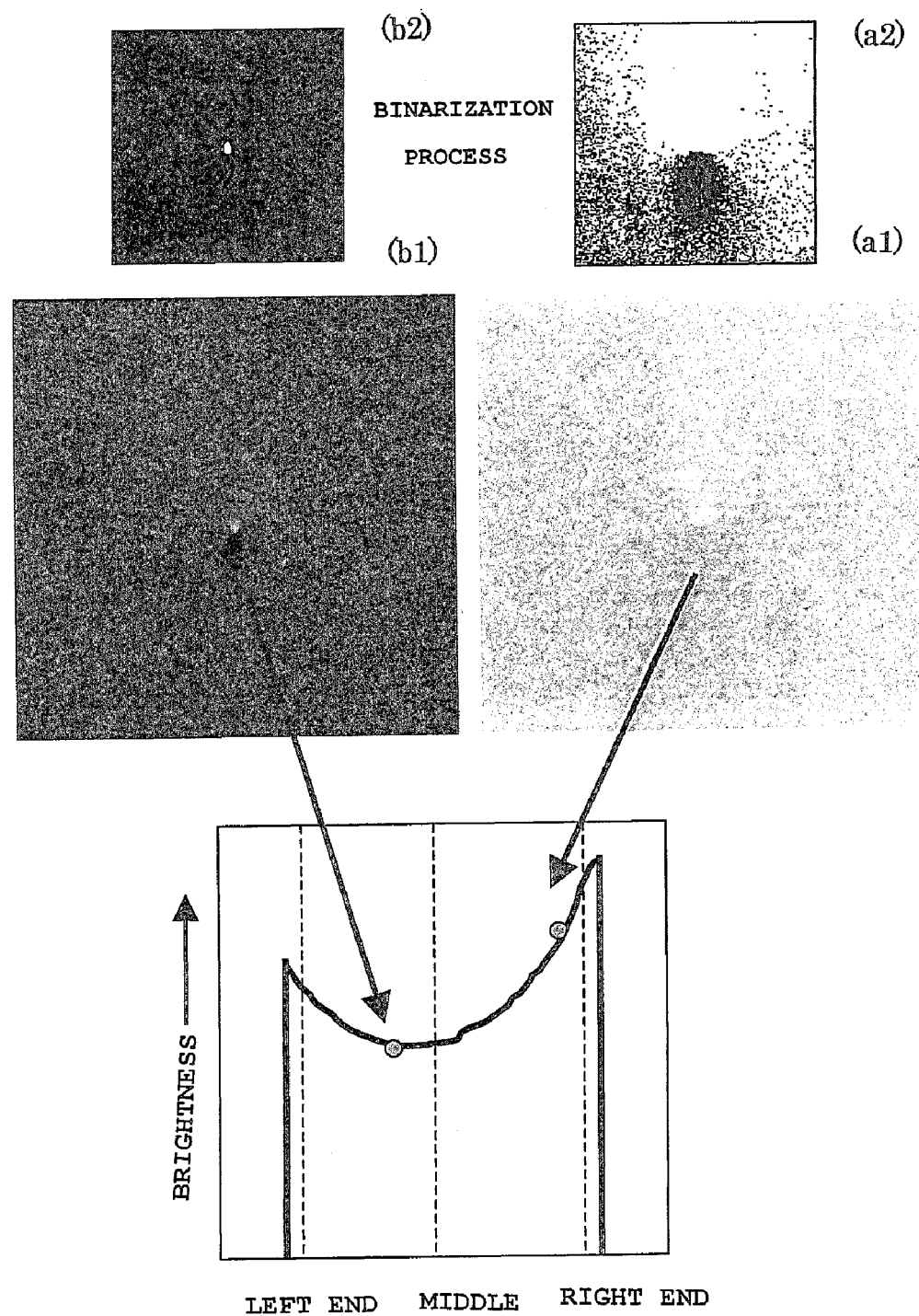
FIG. 9 is a view showing an original image and a binary image in the example of FIG. 6.

The actual image for the case of FIG. 5 is shown in FIG. 8. In FIG. 8, (a1) and (b1) show an original image, and (a2) and (b2) show an image obtained by performing a binarization process on the original image at the periphery of the defect. Since there is no difference in brightness from the central part to the ends, the defect detection can be stably performed. The actual image for the case of FIG. 6 is shown in FIG. 9. In FIG. 9, (a1) shows an original image near the right end, and (a2) shows a binarized image at the periphery of the defect. Since the luminance difference is small between the defect and the periphery thereof, the defect detection is difficult. (b1) shows an original image near the central part, and (b2) shows an image obtained by performing a binarization process on the original image at the periphery of the defect. The defect detection can be performed, but the size differs from the actual size of the defect, and the defect is hard to see.

A comparative experiment of when a polarizing plate protective film (Separator Cerapeel MDA38 manufactured by Toray Advanced Film Co., orientation angle variation of 8.6°) having properties different from those of the retardation layer of the layered film 11 is inserted in place of the inspection retardation filter 16 is carried out. The result is shown in table 2. The numerical values in table 2 show the area (pixel unit) of the defect detected with a method similar to table 1.

TABLE 2

|  | Retardation film | Polarizing plate protective film |
|---|---|---|
| Left end | 21 | 14 |
| Middle | 18 | 0 |
| Right end | 17 | 3 |

It can be recognized that the variation is small in the case of the inspection retardation filter (same as data shown in table 1), but the variation is very large if the polarizing plate protective film is used, and stable defect detection cannot be performed. Since the polarizing plate protective film is ultimately stripped, the orientation angle variation is large compared to that in the retardation layer of the layered film 11. Therefore, the film made of the same material as the relevant protective film does not need to be used for inspection. This is the same for the optical compensation layer of the layered film 11, and the present invention is preferably used for that of small orientation angle variation. The orientation angle variation in this case is preferably smaller than or equal to 4°, and more preferably smaller than or equal to 3°.

<Arrangement Configuration>

An arrangement configuration in the present invention and an arrangement configuration in the comparative example will now be described. According to the configuration of the present invention, the light source 13 is arranged on the lower side of the layered film 11, and the imaging unit 12, the inspection polarization filter 15, and the inspection retardation filter 16 are arranged in such order on the upper side, as shown in FIG. 10(a). Regarding the layered film 11 to be inspected, the polarizing plate 11a is arranged so as to face the light source side, and the retardation layer 11b is arranged so as to face the imaging unit side. The reason is because the influence of retardation is exhibited before the light enters the polarizing plate 11a if the retardation layer 11b is on the light source side, and the variation in brightness cannot be satisfactorily canceled with the filter.

Furthermore, if the filters are immediately above the light source 13, the operation to switch or rotate the filter becomes difficult depending on the type of the inspecting object. For instance, when inspecting the layered film 11 having a length in the width direction of 1500 mm, the task necessary for maintenance such as replacement and rotation becomes greater since the filter becomes larger.

Regarding the comparative examples (b1) to (b6), (b10), and (b11), the inspection polarization filter 15 or the inspection retardation filter 16 is arranged on the light source 13 side. The inspection polarization filter 15 and the inspection retardation filter 16 are constantly inserted and fixed in the light path, and are close to the light source 13, and thus are constantly exposed to light and heat, whereby degradation of the filter by heat energy and light energy tends to easily occur. Therefore, the detection accuracy of the defect also degrades. Such comparative examples might present a possibility of missing minor defects of the layered film 11 due to lack of light quantity since the filter is arranged between the light source 13 and the layered film 11. In order to respond to such problem, the light quantity of the light source 13 can be sufficiently increased, but in turn, leads to increase in power consumption amount and degradation of light source, and furthermore, greater degradation of the filter.

The inspection polarization filter 15 and the inspection retardation filter 16 can be reduced in size by being arranged close to the imaging unit 12 as much as possible, so that the maintenance is facilitated. Therefore, (b1) to (b6), (b10), and (b11) are not preferable in that the inspection polarization filter 15 and the inspection retardation filter 16 are arranged distant from the imaging unit 12. Regarding (b8) and (b9), the inspection retardation filter 16 is arranged to be closer to the imaging unit 12 than the inspection polarization filter 15. Therefore, the light that has passed the retardation layer is polarized by the inspection polarization filter 15 and then entered to the inspection retardation filter 16, and thus cannot be satisfactorily canceled. Regarding comparative example (b7), the arrangement configuration is substantially the same as in the present invention, but the polarizing plate 11a is positioned on the imaging unit 12 side than the retardation layer 11b. Therefore, since influence of the retardation is exhibited before the light enters the polarizing plate 11a if the retardation layer 11b is on the light source side, the variation in brightness cannot be satisfactorily canceled with the filter.

<Data Comparison Related to Temporal Change>

The result of experiment performed on the influence of temporal change will now be described. Comparison between the initial data of the arrangement configuration (same as FIG. 10(a)) of the present invention in which the data shown in FIG. 5 is acquired, and the data after 48 hours is shown in table 3 (left side) and FIG. 10A (upper stage). Similarly, as a comparative example, comparison between the initial data of the arrangement configuration of FIG. 10(b4) and the data after 48 hours is shown in table 3 (right side) and FIG. 10A (lower stage).

TABLE 3

Figure 10:
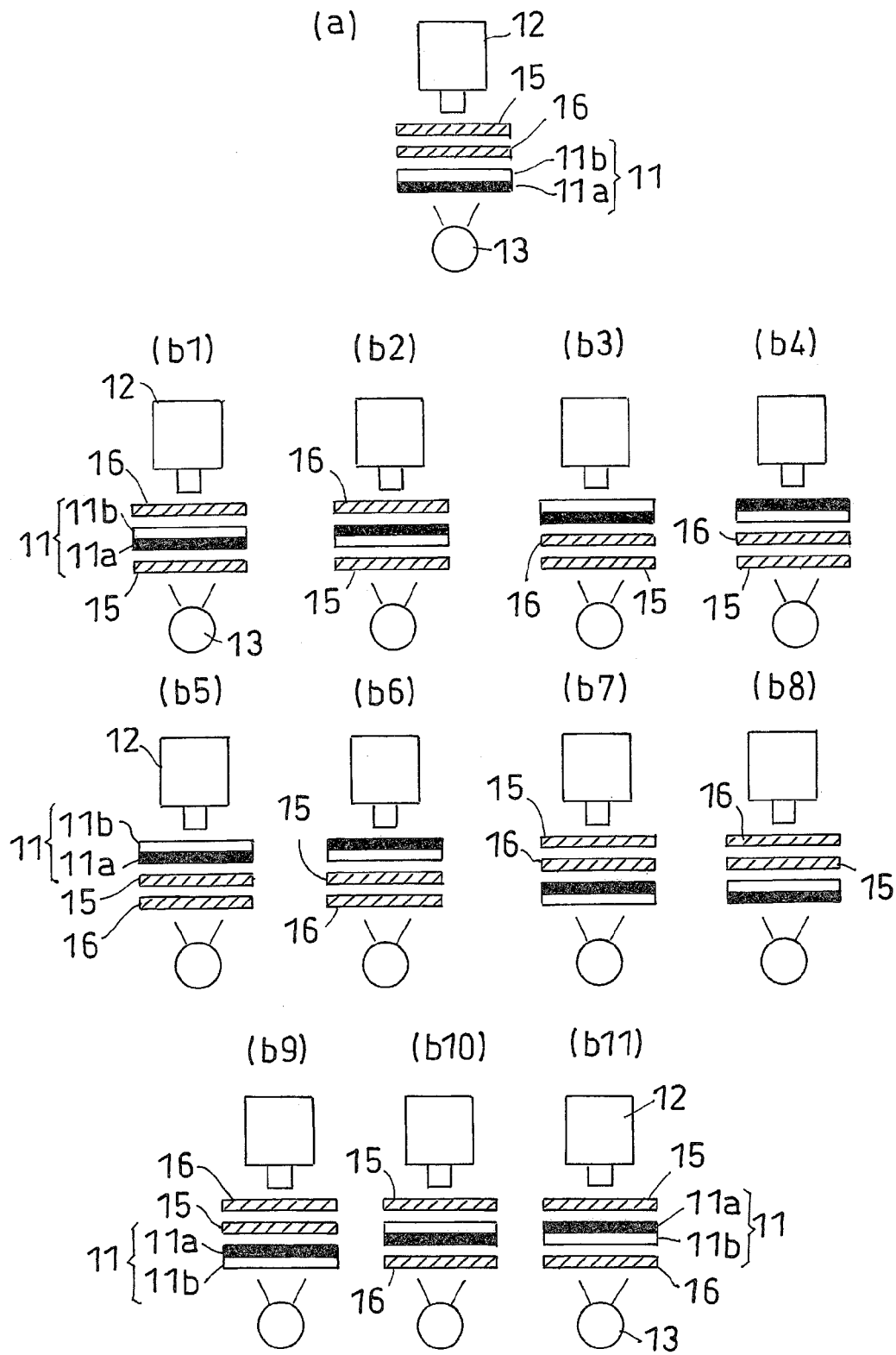
FIG. 10 is a view showing an arrangement configuration of the present invention and an arrangement configuration of a comparative example.
Figure 10A:
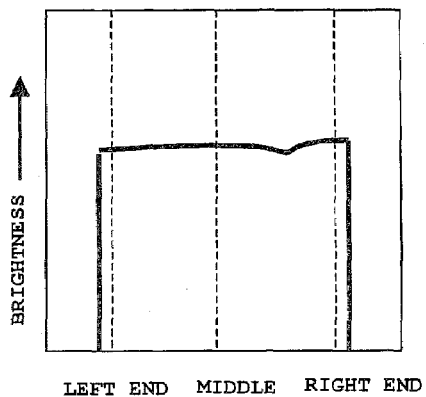
FIG. 10A is a view showing a result of an experiment performed on the influence of temporal change.
Figure 10A:
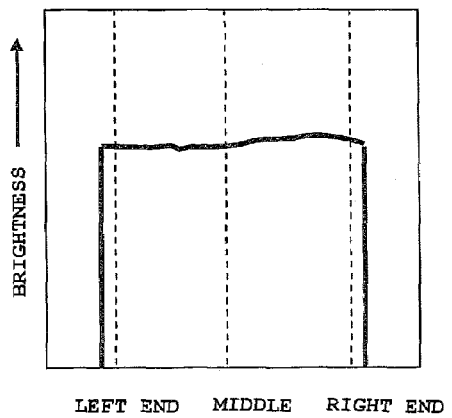
Figure 10A:
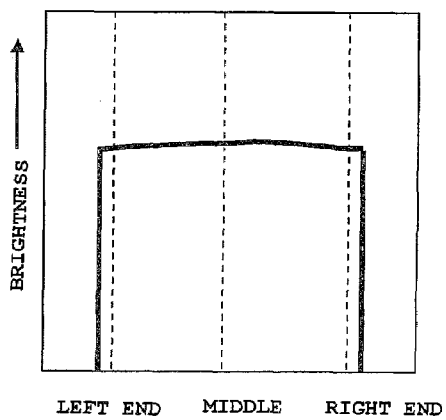
Figure 10A:
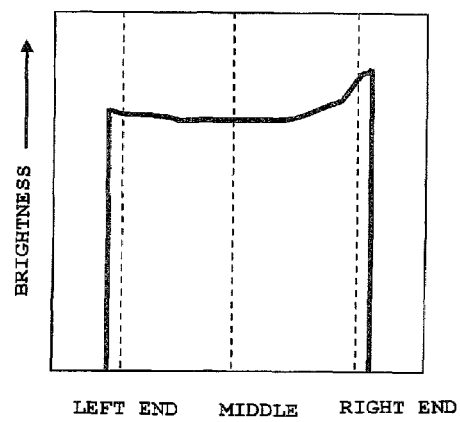

|  | FIG. 5 Initial | FIG. 5 After 48 Hours | FIG. 10 (b4) Initial | FIG. 10 (b4) After 48 Hours |
| --- | --- | --- | --- | --- |
| Left end | 21 | 21 | 20 | 8 |
| Middle | 18 | 20 | 17 | 6 |
| Right end | 17 | 18 | 18 | 0 |

As apparent from such experiment data, degradation of the filter does not occur in the arrangement configuration of the present invention, and thus the accuracy of defect detection can be maintained even after 48 hours have elapsed. In the configuration of FIG. 10(b4), however, degradation of the filter occurs due to heat energy and light energy, and thus defect detection becomes difficult to perform.

The light source used to perform the experiment is halogen light source device MHF-100 (100 Watts) manufactured by Moritex Co., as described above, wherein the brightness of the light source (brightness in measurement at 30 cm above the light source) is adjusted to be 6060 cd/m$^2$.

In the data of FIG. 5, the distance between the light source 13 and the layered film 11 is set to 20 cm, the distance between the layered film 11 and the inspection retardation filter 16 is set to 8 cm, the distance between the inspection retardation filter 16 and the inspection polarization filter 15 is set to 6 cm, and the distance between the inspection polarization filter 15 and the imaging unit 12 is set to 6 cm.

In the data of FIG. 10(b4), the distance between the light source 13 and the inspection polarization filter 15 is set to 6 cm, the distance between the inspection polarization filter 15 and the inspection retardation filter 16 is set to 6 cm, the distance between the inspection retardation filter 16 and the layered film 11 is set to 8 cm, and the distance between the layered film 11 and the imaging unit 12 is set to 20 cm.

<Difference in Imaged Image Due to Arrangement Configuration>

Figure 11:
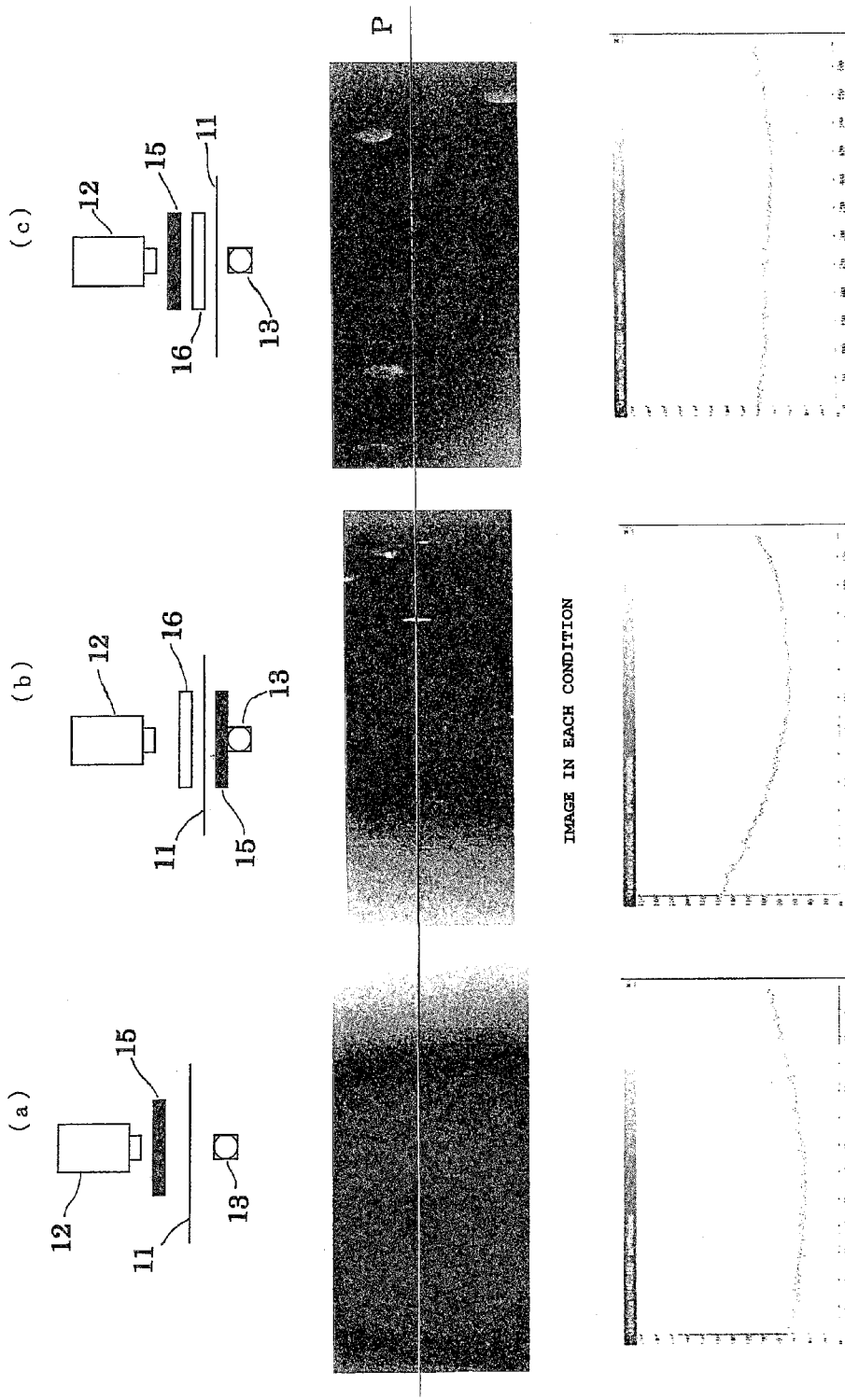
FIG. 11 is a view showing an image imaged in the arrangement configuration of the present invention and an image imaged in the arrangement configuration of the comparative example.

FIG. 11 shows a comparison of a difference in imaged images due to difference in the arrangement configuration. As the layered film 11 to be inspected is used that which the polarizing plate and the retardation layer are layered. FIG. 11(a) shows the arrangement configuration of the prior art, wherein only the inspection polarization filter 15 is arranged, and the inspection retardation filter 16 is not arranged. The arrangement configuration is shown on the upper stage, the actual imaged image is shown on the middle stage, and the luminance distribution along line P of the imaged image is shown on the lower stage. In the case of the prior art, the luminance distribution differs between the central part and the ends. In (b), the inspection retardation filter 16 is arranged on the imaging unit 12 side, and the inspection polarization filter 15 is closely arranged to the light source 13. Looking at the luminance distribution, the luminance variation is larger than that in (a). (c) shows the arrangement configuration of the present invention, it is seen that a substantially uniform brightness is obtained from the central part towards the periphery.

The light source used to perform the experiment is halogen light source device MHF-100 (100 Watts) manufactured by Moritex Co., as described above, wherein the brightness of the light source (brightness in measurement at 30 cm above the light source) is adjusted to be 6060 cd/m$^2$.

Specific dimensional relationship will be described. In FIG. 11(a), the distance between the light source 13 and the layered film 11 is set to 20 cm, the distance between the layered film 11 and the inspection polarization filter 15 is set to 14 cm, and the distance between the inspection polarization filter 15 and the imaging unit 12 is set to 6 cm.

In FIG. 11(b), the light source 13 and the inspection polarization filter 15 are closely attached, wherein the distance between the inspection polarization filter 15 and the layered film 11 is set to 20 cm, the distance between the layered film 11 and the inspection retardation filter 16 is set to 14 cm, and the distance between the inspection retardation filter 16 and the imaging unit 12 is set to 6 cm.

In FIG. 11(c), the distance between the light source 13 and the layered film 11 is set to 20 cm, the distance between the layered film 11 and the inspection retardation filter 16 is set to 8 cm, the distance between the inspection retardation filter 16 and the inspection polarization filter 15 is set to 6 cm, and the distance between the inspection polarization filter 15 and the imaging unit 12 is set to 6 cm.

<Specific Example of Layered Film>

The configuration in which the polarizing plate is layered has been described as an example of the layered film in the present invention, and a specific configuration example will be further described below. The polarizing plate is formed to a long band shape, and the polarizing plate of respective size is obtained by being punched out from a polarizing plate original fabric of film shape. The polarizing plate original fabric is obtained by laminating a TAC film (protective film) etc. on both front and back sides of the PVA film (polarizer) fabricated in advance. The defect (scratches, foreign substances, etc.) on the surface or on the inside of the polarizing plate original fabric N having a multi-layered structure needs to be detected.

The polarizing plate original fabric N is fabricated with a fabrication method including (A) step of drying a polyvinyl alcohol film subjected to dying, crosslinking and stretching processes, and obtaining a polarizer; (B) step of laminating a protective layer on one side or on both sides of the polarizer; and (C) step of performing heating process after laminating.

The respective processes of dying, crosslinking, and stretching of the polyvinyl alcohol film do not need to be separately performed and may be simultaneously performed, or the order of each process may be arbitrary. The polyvinyl alcohol film subjected to swelling process may be used for the polyvinyl alcohol film. Generally, the polyvinyl alcohol film is immersed in a solution containing iodine and dichroic dye to be dyed by attracting the iodine and the dichroic dye, and then washed, uniaxially stretched to a stretching magnification of three to seven times in a solution containing boric acid and pyroborate, and then dried. After stretching in the solution containing iodine and dichroic dye, the film is further stretched (two-stage stretching) in the solution containing boric acid and pyroborate, and thereafter dried, so that the orientation of iodine enhances and polarization degree improves, and thus it is particularly preferable.

The polyvinyl alcohol polymer includes those saponified after polymerizing vinyl acetate, those in which a small amount of copolymerizable monomers such as unsaturated carboxylic acid, unsaturated sulfonic acid, cation monomer etc. is copolymerized to the vinyl acetate, and the like. The average polymerization degree of the polyvinyl alcohol polymer is not particularly limited and may be an arbitrary value, but is preferably greater than or equal to 1000, and more preferably between 2000 and 5000. The saponification degree of the polyvinyl alcohol polymer is preferably greater than or equal to 85 mol % and more preferably between 98 and 100 mol %.

The thickness of the polarizer to be fabricated is generally between 5 and 80 µm, but is not limited thereto, and the method for adjusting the thickness of the polarizer is not particularly limited, wherein usual methods using tenter, roll stretching, rolling etc. may be used.

An adhering process of the polarizer and the polarizer protective film is not particularly limited, but is performed by way of adhesive including vinyl alcohol polymer, adhesive including at least water-soluble crosslinking agent of vinyl alcohol polymer such as boric acid and pyroborate, glutaraldehyde and melamine, oxalic acid, and the like, etc. The adhesive layer is formed as an applied dry layer etc. of aqueous solution, but other additives and catalysts such as acid can also be optionally compounded in preparing the aqueous solution.

An appropriate transparent film can be used for the polarizer protective film arranged on one side or both sides of the polarizer. Among them, a film made of polymer excellent in transparency, mechanical strength, heat stability, moisture shielding property, and the like is preferably used. The polymer includes acetate resin such as triacetyl cellulose, polycarbonate resin, polarylate, polyester resin such as polyethylene telephtalate, polyimide resin, polysulfone resin, polyether sulfone resin, polystylene resin, polyethylene, polyolefin resin such as polypropylene, polyvinyl alcohol resin, polyvinyl chloride resin, polynorbornene resin, polymethyl methacrylate resin, liquid crystal polymer, and the like. The film may be fabricated with any one of casting method, calendar method, and extrusion method.

The polymer film disclosed in Japanese Laid-Open Patent Publication No. 2001-343529 (WO01/37007), such as resin composition containing (A) thermoplastic resin having substituted and/or unsubstituted imide group on the side chain, and (B) thermoplastic resin having substituted and/unsubstituted phenyl and nitrile group on the side chain, are listed. Specific examples include a film of resin composition containing alternate copolymer including isobutylene and N-methyl maleimide, and acrylonitrile-styrene copolymer. The film may be a film formed by a mixed extrudate of the resin composition. Such films have small retardation, and small photoelastic coefficient, and thus drawbacks such as unevenness due to strain of the polarizing plate can be resolved, and furthermore, excellent humidification durability is obtained since the moisture permeability is small.

Furthermore, the polarizer protective film is preferably not colored as much as possible. Therefore, a protective film in which the retardation value in the film thickness direction expressed as $Rth=[(nx+ny)/2-nz] \cdot d$ (wherein nx, ny are main index of refraction in film surface, nz is an index of refraction in the film thickness direction, and d is film thickness) is between −90 nm and +90 nm is preferably used. The coloring (optical coloring) of the polarizing plate caused by the polarizer protective film can be substantially resolved by using that whose retardation value (Rth) in the thickness direction is between −90 nm and +90 nm. The retardation value (Rth) in the thickness direction is more preferably between −80 nm and +80 nm, and particularly between −70 nm and +70 nm.

From the standpoints of polarizing characteristics and durability, acetate resin such as triacetyl cellulose is preferable, and in particular, triacetyl cellulose film whose surface is saponification processed with alkali etc. is preferable. When arranging the polarizer protective film on both sides of the layered film, the polarizer protective film including different polymers may be used on the front and the back. The thickness of the polarizer protective film is arbitrary, but is generally less than or equal to 500 µm, preferably between 1 to 300 µm, and more preferably between 5 and 200 µm in an aim of thinning the polarizing plate.

Regarding the optical compensation layer to be layered with the polarizing plate, the present invention can be applied to a surface treated layer, optical layer, retardation film, and orientation liquid crystal layer. As the retardation filter used in this case may be conveniently used that having the same configuration as the optical compensation layer, but may be used the filter having the same optical characteristics as the optical compensation layer. In the present invention, it is particularly effectively used in the optical compensation layer including an orientation layer of discotic liquid crystal and a retardation film.

The polarizer protective film may be subjected to hard coating process, antireflection process, and process targeting prevention of sticking, diffusion, anti-glare and the like. The hard coating process is performed in an aim of preventing scratches on the surface of the polarizing plate, and may be formed with a method for adding a curing membrane excellent in hardness, slipping property, and the like by an appropriate ultraviolet curable resin of silicone series etc. to the surface of the transparent protective layer.

The antireflection process is performed in an aim of preventing reflection of outside light at the surface of the polarizing plate and is achieved by forming an antireflection film in accordance with the prior art. The sticking prevention is performed in an aim of preventing close attachment to an adjacent layer, and the anti-glare process is performed in an aim of preventing the outside light from reflecting at the surface of the polarizing plate and inhibiting the visibility of the transmitted light of the polarizing plate, and they are achieved by providing a microscopic concave-convex structure on the surface of the transparent protective layer with an appropriate method such as coarse surface manner by sandblast manner, emboss processing manner, and the like or a manner of compounding transparent fine particles, and the like.

The layered film according to the present invention is used as an optical film by layering various optical layers in practical use. The optical layer is not particularly limited, but includes a method for performing hard coating process, antireflection process, and surface treatment in an aim of preventing sticking or diffusion and antiglare, or layering an orientation liquid crystal layer in an aim of compensating viewing angle etc. with respect to a surface (surface not arranged with the adhesive application layer) on which the polarizer of the transparent protective layer is not adhered. The film in which one or two and more optical films used for forming the liquid crystal display device etc. such as reflection plate, semi-transmissive plate, retardation film (including wavelength plate ($\lambda$ plate) such as ½ and ¼), viewing angle compensation film, and the like are laminated may be used. In particular, if the sheet-form product is the polarizing plate, it is preferably applied as reflective polarizing plate or semi-transmissive polarizing plate formed by layering the reflective plate or the semi-transmissive reflection plate; elliptical polarizing plate or circular polarizing plate formed by layering the retardation film; wide viewing angle polarizing plate formed by layering the viewing angle compensation layer or the viewing angle compensation film; or polarizing plate formed by layering luminance enhancement film.

The reflective polarizing plate has a reflection layer arranged on the polarizing plate, and is used to form a liquid crystal display device etc. of a type for displaying by reflecting the incident light from the viewing side (display side), wherein it has advantages that incorporation of a light source such as backlight can be omitted and that thinning of liquid crystal display device can be achieved. The reflective polarizing plate is formed with an appropriate manner such as a manner for attaching a reflection layer made of metal etc. on one side of the polarizing plate via the transparent protective layer etc. if necessary.

The semi-transmissive polarizing plate can be obtained as a reflection layer of semi-transmissive type such as half mirror for reflecting and transmitting the light by the reflection layer. The semi-transmissive polarizing plate is normally arranged on the back side of the liquid crystal cell, and can form a liquid crystal display device etc. of a type of displaying the image by reflecting the incident light from the viewing side (display side) when using the liquid crystal display device etc. in a relatively bright atmosphere, and displaying the image by using an incorporating light source such as backlight incorporated on the back side of the semi-transmissive polarizing plate when using the device in a relatively dark atmosphere. In other words, the semi-transmissive polarizing plate is useful for forming the liquid crystal display device etc. of a type that can save energy in use of light source such as back light under a bright atmosphere, and that can use an incorporating light even under a relatively dark atmosphere.

The elliptical polarizing plate or the circular polarizing plate formed by further layering the retardation film on the polarizing plate will now be described. The retardation film etc. is used when changing the linear polarized light to elliptical polarized light or circular polarized light, changing the elliptical polarized light or circular polarized light to linear polarized light, or changing the polarizing direction of the linear polarized light. In particular, a so-called ¼ wavelength plate (also referred to as $\lambda/4$ plate) is used as the retardation film for changing the linear polarized light to circular polarized light or changing the circular polarized light to linear polarized light. The ½ wavelength plate (also referred to as $\lambda/2$ plate) is normally used when changing the polarizing direction of the linear polarized light.

The elliptical polarizing plate is effectively used to compensate (prevent) coloring (blue or black) caused by birefringence of the liquid crystal layer of the super twist nematic (STN) liquid crystal display device, and displaying in black and white without color. Furthermore, that in which a three-dimensional refraction index is controlled is preferable in that coloring that occurs when viewing the screen of the liquid crystal display device from a diagonal direction can also be compensated (prevented). The circular polarizing plate is effectively used when adjusting the color tone of the image of the reflection type liquid crystal display device in which the image is color displayed, and also has an antireflection function.

The retardation film includes a birefringence film formed by uniaxial or biaxial stretch processing a polymer raw material, an orientation film of a liquid crystal polymer, a film in which the orientation layer of the liquid crystal polymer is supported by a film, and the like. The stretching process is performed with a roll stretching method, long gap stretching method, tentar stretching method, tubular stretching method, and the like. The stretching magnification is generally about 1.1 to 3 times in the uniaxial stretching. The thickness of the retardation film is also not particularly limited, but is generally between 10 and 200 µm, and preferably between 20 and 100 µm.

The polymer material includes polyvinyl alcohol, polyvinyl butyral, polymethyl vinyl ether, polyhydroxyethyl acrylate, hydroxyethyl cellulose, hydroxypropyl cellulose, methyl cellulose, polycarbonate, polyarylate, polysulfone, polyethylene telephtalate, polyethylene naphtalate, polyether sulfone, polyphenyl sulfide, polyphenylene oxide, polyaryl sulfone, polyvinyl alcohol, polyamide, polyimide, polyolefin, polyvinyl chloride, cellulose polymer, or various copolymers of binary series and ternary series, graft copolymer, blended article of the above, and the like. The polymer raw material becomes the orientated object (stretched film) by stretching and the like.

The liquid crystal polymer includes various types of principle chain type or side chain type in which the conjugated linear atom group (mesogen) that provides liquid crystal orientation is introduced to the principle chain or the side chain of the polymer. Specific examples of the liquid crystal polymer of principle chain type include polyester liquid crystal polymer, discotic polymer, colesteric polymer and the like of nematic orientation having a structure in which the mesogenic group is bonded at the spacer part that provides bendability. Specific examples of the liquid crystal polymer of side chain type include those which include a mesogen part including a para substitution annular compound unit that provides nematic orientation via a spacer part having polysiloxane, polyacrylate, polymethacrylate, or polymalonate as the principle chain framework and conjugate atomic group as the side chain. The liquid crystal polymers are obtained by developing and heat treating a solution of liquid crystal polymer on the orientation processing surface such as that in which the surface of the thin film of polyimide, polyvinyl alcohol etc. formed on the glass substrate is subjected to rubbing process, and that in which silicon oxide is oblique vapor deposited.

The retardation film may have an appropriate retardation depending on the usage purpose such as purpose of compensating coloring, viewing angle, and the like by birefringence of various wavelength plates and liquid crystal layer, or may have optical characteristics such as retardation controlled by layering two or more types of retardation film.

The polarizing plate in which the polarizing plate and the luminance enhancement film are laminated is normally used by being arranged on the back side of the liquid crystal cell. The luminance enhancement film has characteristics in reflecting linear polarized light of a predetermined polarizing axis or circular polarized light of a predetermined direction when natural light enters by back light of the liquid crystal display device etc. or by reflection from the back side, and transmitting other lights, wherein the polarizing plate in which the luminance enhancement film is layered with the polarizing plate transmits the light from the light source such as the back light to obtain the transmitted light of a predetermined polarization state, and reflects lights other than in the predetermined polarization state without transmitting. The light reflected by the luminance enhancement film surface is inverted via a reflection layer etc. arranged further on the rear side thereof to again enter the luminance enhancement film, wherein some or all of the lights are transmitted as light of a predetermined polarization state to increase the light quantity to be transmitted through the luminance enhancement film, and the polarized light less likely to be absorbed by the polarizer is supplied to increase the light quantity that can be used in the liquid crystal display image display etc. thereby enhancing luminance.

The layered film of the present invention may be formed by layering the polarizing plate or two layers of or three or more layers of optical layers as in a polarization separation polarizing plate. Therefore, the reflection type elliptical polarizing plate, the semi-transmissive type elliptical polarizing plate, and the like in which the reflective polarizing plate or the semi-transmissive polarizing plate is combined with the retardation film may be used.

The optical film in which the optical layer is layered on the polarizing plate may be formed with a manner of sequential and separate layering in the fabrication process of the liquid crystal display device and the like, but the optical film obtained by being layered in advance is advantageous in that it is excellent in stability of the quality, assembly work, etc. and enhances the fabrication step of the liquid crystal display device, and the like. An appropriate adhering means such as adhesive layer may be used for layering. In adhering the above described polarizing plate and another optical layer, the optical axes thereof have an appropriate arrangement angle depending on the target retardation characteristics, and the like.

An adhesive layer for adhering with another member such as liquid crystal cell may be arranged on the polarizing plate according to the present invention or the layered optical member. The adhesive layer is not particularly limited, and may be formed with an appropriate adhesive in accordance with the prior art such as acryl series. In view of preventing foaming phenomenon and stripping phenomenon by moisture absorption, lowering of optical characteristics by thermal expansion difference, preventing warp of the liquid crystal cell, and furthermore, forming the image display device having high quality and excellent in durability, the adhesive layer having low moisture absorptivity and excellent in heat resistance is preferable. The adhesive layer containing fine particles and providing light diffusability may be used. The adhesive layer merely needs to be arranged on the required surface if necessary, and the adhesive layer may be arranged on one side or on both sides of the protective layer with respect to the polarizing plate including the polarizer and the protective layer.

The exposed surface of the adhesive layer is temporarily attached with the separator and covered in an aim of preventing pollution etc. until supplied for practical use. Thus, contact to the adhesive layer in the usual handling state is prevented. The separator obtained by performing coating process on a translucent plastic film such as polyester and polyethylene telephtalate with an appropriate stripping agent such as silicone or long chain alkyl, fluorine or molybdenum sulfide may be used. An easy stripping protective film in which the adhesive layer is layered on the translucent plastic film may be temporarily attached to the surface of the layered film without the adhesive layer, thereby protecting the layered film.

In the present invention, ultraviolet absorption ability may be provided to the polarizer, the transparent protective layer, the optical film, or the like forming the polarizing plate, and each layer such as adhesive layer with manners such as a manner of processing with ultraviolet absorber such as ester salicylate compound, benzophenol compound, benzotriazole compound, cyanoacrylate compound, nickel complex salt compound, and the like.

The layered film according to the present invention is preferably used in forming a liquid crystal display device, an organic EL display device, and an image display device such as PDP.

The polarizing plate or the optical film of the present invention can be preferably used for forming various devices such as a liquid crystal display device. The liquid crystal display device is formed in accordance with the prior art. In other words, the liquid crystal display device is generally formed by appropriately assembling the liquid crystal cell, the polarizing plate or the optical film, and optional components of the illumination system etc., and incorporating a drive circuit, but is not particularly limited in the present invention other than that the polarizing plate or the optical film according to the present invention is used, and is in accordance with the prior art. With regards to the liquid crystal cell, an arbitrary type such as TN type, STN type, $\pi$ type, or the like may be used.

The liquid crystal display device in which the polarizing plate or the optical film is arranged on one side or both sides of the liquid crystal cell, or an appropriate liquid crystal display device using a backlight or a reflection plate in the illumination system may be formed. In this case, the polarizing plate or the optical film of the present invention may be arranged on one side or both sides of the liquid crystal cell. When arranging the polarizing plate or the optical film on both sides, they may be the same or different. Furthermore, when forming the liquid crystal display device, an appropriate component such as a diffusion plate, an antiglare layer, an antireflection film, a protective plate, a prism array, a lens array sheet, a light diffusion plate, a backlight, or the like may be arranged at an appropriate position for one or two or more layers.

An organic electroluminescence device (organic EL display device) will now be described. Generally, the organic EL display device forms a light emitting body (organic electroluminescence light emitting body) by layering in order a transparent electrode, an organic light emitting layer, and a metal electrode on a transparent substrate. The organic light emitting layer is known as a layered body of various organic thin films, and a configuration of various combinations such as a layered body including a hole injection layer containing triphenylamine derivative etc., and a light emitting layer containing fluorescence organic solid of anthracene etc.; layered body including such light emitting layer and electron injection layer containing perylene derivative; and layered body including such hole injection layer, light emitting layer, and electron injection layer may be adopted.

In the organic EL display device including the organic electroluminescence light emitting body having a transparent electrode on the front surface side of the organic light emitting layer that emits light by voltage application and a metal electrode on the back surface side of the organic light emitting layer, the polarizing plate is arranged on the front surface side of the transparent electrode, and the retardation film is arranged between the transparent electrode and the polarizing plate.

Since the retardation film and the polarizing plate act to polarize the light entered from the outside and reflected by the metal electrode, they have an effect of preventing the mirror finished surface of the metal electrode from becoming visible from the outside by such polarization action. In particular, the mirror finished surface of the metal electrode can be completely shielded by forming the retardation film with the ¼ wavelength plate, and adjusting the angle formed in the polarizing direction by the polarizing plate and the retardation film to π/4.

The layered film according to the present invention can be preferably used for forming various devices such as a liquid crystal display device. The liquid crystal display device is formed with an appropriate configuration in accordance with the prior art of transmissive type, reflective type, or transmissive-reflective type by arranging the layered film (e.g., polarizing plate) according to the present invention on one side or on both sides of the liquid crystal cell. Therefore, the liquid crystal cell forming the liquid crystal display device is arbitrary, and the liquid crystal cell of an appropriate type such as simple matrix drive type represented by a thin-film transistor may be used.

According to the present invention, when performing defect inspection of the layered film including the polarizing plate and the optical compensation layer (retardation film or TAC with discotic liquid crystal) by using the inspection polarization filter and the inspection retardation filter (inspection retardation filter and inspection discotic liquid crystal layer), stable defect detection can be performed by arranging the inspection polarization filter and the inspection retardation filter to be arranged on the imaging light path in an appropriate order.

The cross sectional structure of the layered film 11 is shown in FIG. 12, but the present invention is not limited to the illustrated layer structure.

The invention claimed is:

1. A layered film fabrication method comprising the steps of fabricating a layered film by layering at least a polarizing plate and an optical compensation layer, and performing defect inspection of the fabricated layered film; wherein the defect inspection step includes the steps of
irradiating a light on the layered film from a light source arranged on the polarizing plate layered side of the layered film,
imaging a transmitted light image of the layered film by an imaging unit arranged on the optical compensation layer side of the layered film, and
detecting a defect existing in the layered film based on the transmitted light image imaged by the imaging unit; and
the imaging by the imaging unit is performed via an inspection polarization filter arranged adjacent to the imaging unit on a light path between the light source and the imaging unit, and an inspection retardation filter arranged between the inspection polarization filter and the layered film on the light path between the light source and the imaging unit;
wherein the inspection retardation filter cancels the retardation of the optical compensation layer.

2. A defect detection method of a layered film in which at least a polarizing plate and an optical compensation layer are layered; the method comprising the steps of:
irradiating a light on the layered film from a light source arranged on the polarizing plate layered side of the layered film;
imaging a transmitted light image of the layered film by an imaging unit arranged on the optical compensation layer side of the layered film; and
detecting a defect existing in the layered film based on the transmitted light image imaged by the imaging unit; wherein
the imaging by the imaging unit is performed via an inspection polarization filter arranged adjacent to the imaging unit on a light path between the light source and the imaging unit, and an inspection retardation filter arranged between the inspection polarization filter and the layered film on the light path between the light source and the imaging unit;
wherein the inspection retardation filter cancels the retardation of the optical compensation layer.

3. A defect detection device of a layered film in which at least a polarizing plate and an optical compensation layer are layered; the device comprising:
a light source arranged on the polarizing plate layered side of the layered film and irradiating a light on the layered film;
an imaging unit arranged on the optical compensation layer side of the layered film and imaging a transmitted light image of the layered film;
a defect detection unit for detecting a defect existing in the layered film based on the transmitted light image imaged by the imaging unit;
an inspection polarization filter arranged adjacent to the imaging unit on a light path between the light source and the imaging unit; and
an inspection retardation filter arranged between the inspection polarization filter and the layered film on the light path between the light source and the imaging unit.

4. The layered film defect detection device according to claim 3, wherein the optical compensation layer is a retardation layer having an orientation angle variation of retardation controlled to be within 4°, and the inspection retardation filter has same characteristics as the retardation layer.

5. The layered film defect detection device according to claim 3, wherein the optical compensation layer includes a discotic liquid crystal layer, and the inspection retardation filter is an inspection discotic liquid crystal layer being the same in material thickness or retardation as the optical compensation layer.

6. The layered film defect detection device according to claim 3, further comprising a first optical axis adjustment unit for adjusting a relative angle position of a polarizing axis of the inspection polarization filter and a polarizing axis of the polarizing plate, whereby the position of the inspection polarization filter is controlled.

7. The layered film defect detection device according to claim 3, further comprising a second optical axis adjustment unit for adjusting a relative angle position of an optical axis of the inspection retardation filter and an optical axis of the optical compensation layer, whereby the position of the inspection polarization filter is controlled.

* * * * *